United States Patent [19]

Sumi et al.

[11] Patent Number: 5,463,025
[45] Date of Patent: Oct. 31, 1995

[54] PROTEIN HAVING HUMAN PLASMIN INHIBITING ACTIVITY

[75] Inventors: Yoshihiko Sumi, Hino; Yataro Ichikawa, Tokorozawa; Nobuo Aoki, Tokyo; Masami Muramatsu, Tokorozawa, all of Japan

[73] Assignee: Teijin Limited, Japan

[21] Appl. No.: 185,162

[22] Filed: Jan. 24, 1994

Related U.S. Application Data

[63] Continuation of Ser. No. 60,691, May 13, 1993, abandoned, which is a continuation of Ser. No. 419,913, Sep. 5, 1989, abandoned.

[30] Foreign Application Priority Data

Sep. 5, 1988 [JP] Japan ................... 63-220437

[51] Int. Cl.$^6$ .................... C07K 14/47; A61K 38/17
[52] U.S. Cl. .................... 530/380; 530/381; 530/382; 435/69.2
[58] Field of Search .................... 530/350, 380, 530/381, 382, 395; 435/69.2, 212; 514/2, 8, 12, 21; 424/94.64

[56] References Cited

U.S. PATENT DOCUMENTS 4,346,029  8/1982  Collen et al. ................... 530/392

FOREIGN PATENT DOCUMENTS 0257630  3/1988  European Pat. Off. .
0272609  6/1988  European Pat. Off. .

OTHER PUBLICATIONS

Sakata et al. (1980) J. Clin. Invest 65, 290–297.
Reed et al. (1990) Circulation 82, 164–168; Abstract Only.
Holmes et al. (1987) Biochemistry 26, 5133–5140.
Christensen et al. (1992) FEBS Lett. 312(1), 100–104.
Tone et al. (1987) J. Biochem. 102, 1033–1041.
Holmes et al. (1987) J. Biol. Chem. 262, 1659–1664.
Sumi et al., "J. Biochemistry" 106 (4) 703–707 (1989).
Sumi et al., "J. Cellular Biochemistry Suppl.", Vol. 0, Part 13A, p. 95 Jan. 1989, Abst. A338.

*Primary Examiner*—Charles L. Patterson, Jr.
*Attorney, Agent, or Firm*—Wenderoth, Lind & Ponack

[57] ABSTRACT

A protein having human plasmin inhibiting activity, substantially equivalent reactivity with human plasmin to a human $\alpha_2$-plasmin inhibitor derived from plasma, a binding ability to human fibrin about ¼ to about ⅓ of that of the human $\alpha_2$-plasmin inhibitor derived from plasma, and a molecular weight of about 50,000 to about 77,000.

7 Claims, 14 Drawing Sheets

FIG. IA

```
1                        10                        20
MetGluProLeuGlyArgGlnLeuThrSerGlyProAsnGlnGluGlnValSerProLeu
                         30                        40
ThrLeuLeuLysLeuGlyAsnGlnGluProGlyGlyGlnThrAlaLeuLysSerProPro
                         50                        60
GlyValCysSerArgAspProThrProGluGlnThrHisArgLeuAlaArgAlaMetMet
                         70                        80
AlaPheThrAlaAspLeuPheSerLeuValAlaGlnThrSerThrCysProAsnLeuIle
                         90                        100
LeuSerProLeuSerValAlaLeuAlaLeuSerHisLeuAlaLeuGlyAlaGlnAsnHis
                         110                       120
ThrLeuGlnArgLeuGlnGlnValLeuHisAlaGlySerGlyProCysLeuProHisLeu
                         130                       140
LeuSerArgLeuCysGlnAspLeuGlyProGlyAlaPheArgLeuAlaAlaArgMetTyr
                         150                       160
LeuGlnLysGlyPheProIleLysGluAspPheLeuGluGlnSerGluGlnLeuPheGly
                         170                       180
AlaLysProValSerLeuThrGlyLysGlnGluAspAspLeuAlaAsnIleAsnGlnTrp
                         190                       200
ValLysGluAlaThrGluGlyLysIleGlnGluPheLeuSerGlyLeuProGluAspThr
                         210                       220
ValLeuLeuLeuLeuAsnAlaIleHisPheGlnGlyPheTrpArgAsnLysPheAspPro
                         230                       240
SerLeuThrGlnArgAspSerPheHisLeuAspGluGlnPheThrValProValGluMet
                         250                       260
MetGlnAlaArgThrTyrProLeuArgTrpPheLeuLeuGluGlnProGluIleGlnVal
                         270                       280
AlaHisPheProPheLysAsnAsnMetSerPheValValLeuValProThrHisPheGlu
                         290                       300
TrpAsnValSerGlnValLeuAlaAsnLeuSerTrpAspThrLeuHisProProLeuVal
                         310                       320
TrpGluArgProThrLysValArgLeuProLysLeuTyrLeuLysHisGlnMetAspLeu
                         330                       340
ValAlaThrLeuSerGlnLeuGlyLeuGlnGluLeuPheGlnAlaProAspLeuArgGly
                         350                       360
IleSerGluGlnSerLeuValValSerGlyValGlnHisGlnSerThrLeuGluLeuSer
```

FIG. IB

```
                370                                           380
GluValGlyValGluAlaAlaAlaAlaThrSerIleAlaMetSerArgMetSerLeuSer 390                                           400
SerPheSerValAsnArgProPheLeuPhePheIlePheGluAspThrThrGlyLeuPro 410                                           420
LeuPheValGlySerValArgAsnProAsnProSerAlaProArgGluLeuLysGluGln 430                                           440
GlnAspSerProGlyAsnLysAspPheLeuGlnSerLeuLysGlyPheProArgGlyAsp 450                                           460
LysLeuPheGlyProAspLeuLysLeuValProProMetGluGluAspTyrProGlnPhe

464
GlySerProLys
```

FIG. 2A

```
         10         20         30         40         50         60
ATGGAGCCCTTGGGCCGGCAGCTAACTAGCGGGCCGAACCAGGAGCAGGTGTCCCCACTT
MetGluProLeuGlyArgGlnLeuThrSerGlyProAsnGlnGluGlnValSerProLeu 70         80         90        100        110        120
ACCCTCCTCAAGTTGGGCAACCAGGAGCCTGGTGGCCAGACTGCCCTGAAGAGTCCCCCA
ThrLeuLeuLysLeuGlyAsnGlnGluProGlyGlyGlnThrAlaLeuLysSerProPro 130        140        150        160        170        180
GGAGTCTGCAGCAGAGACCCCACCCCAGAGCAGACCCACAGGCTGGCCCGGGCCATGATG
GlyValCysSerArgAspProThrProGluGlnThrHisArgLeuAlaArgAlaMetMet 190        200        210        220        230        240
GCCTTCACTGCCGACCTGTTCTCCCTGGTGGCTCAAACGTCCACCTGCCCCAACCTCATC
AlaPheThrAlaAspLeuPheSerLeuValAlaGlnThrSerThrCysProAsnLeuIle 250        260        270        280        290        300
CTGTCACCCCTGAGTGTGGCCCTGGCGCTGTCTCACCTGGCACTAGGTGCTCAGAACCAC
LeuSerProLeuSerValAlaLeuAlaLeuSerHisLeuAlaLeuGlyAlaGlnAsnHis 310        320        330        340        350        360
ACGTTGCAGAGGCTGCAACAGGTGCTGCACGCAGGCTCAGGGCCCTGCCTCCCCCATCTG
ThrLeuGlnArgLeuGlnGlnValLeuHisAlaGlySerGlyProCysLeuProHisLeu 370        380        390        400        410        420
CTGAGCCGCCTCTGCCAGGACCTGGGCCCCGGCGCGTTCCGACTGGCTGCCAGGATGTAC
LeuSerArgLeuCysGlnAspLeuGlyProGlyAlaPheArgLeuAlaAlaArgMetTyr 430        440        450        460        470        480
CTGCAGAAAGGATTTCCCATCAAAGAAGATTTCCTGGAACAATCCGAACAGCTATTTGGG
LeuGlnLysGlyPheProIleLysGluAspPheLeuGluGlnSerGluGlnLeuPheGly 490        500        510        520        530        540
GCAAAGCCCGTGAGCCTGACGGGAAAGCAGGAAGATGACCTGGCAAACATCAACCAATGG
AlaLysProValSerLeuThrGlyLysGlnGluAspAspLeuAlaAsnIleAsnGlnTrp 550        560        570        580        590        600
GTGAAGGAGGCCACGGAGGGGAAGATTCAGGAATTCCTCTCTGGGCTGCCGGAAGACACC
ValLysGluAlaThrGluGlyLysIleGlnGluPheLeuSerGlyLeuProGluAspThr 610        620        630        640        650        660
GTGTTGCTTCTCCTCAACGCCATCCACTTCCAGGGTTTCTGGAGGAACAAGTTTGACCCG
ValLeuLeuLeuLeuAsnAlaIleHisPheGlnGlyPheTrpArgAsnLysPheAspPro 670        680        690        700        710        720
AGCCTTACCCAGAGAGACTCCTTCCACCTGGACGAGCAGTTCACGGTGCCCGTGGAAATG
SerLeuThrGlnArgAspSerPheHisLeuAspGluGlnPheThrValProValGluMet 730        740        750        760        770        780
ATGCAGGCCCGCACGTACCCGCTGCGCTGGTTCTTGCTGGAGCAGCCTGAGATCCAGGTG
MetGlnAlaArgThrTyrProLeuArgTrpPheLeuLeuGluGlnProGluIleGlnVal
```

FIG. 2B

```
           790       800       810       820       830       840
GCTCATTTCCCCTTTAAGAACAACATGAGCTTTGTGGTCCTTGTACCCACCCACTTTGAA
AlaHisPheProPheLysAsnAsnMetSerPheValValLeuValProThrHisPheGlu 850       860       870       880       890       900
TGGAACGTGTCCCAGGTACTGGCCAACCTGAGTTGGGACACCCTGCACCCACCTCTGGTG
TrpAsnValSerGlnValLeuAlaAsnLeuSerTrpAspThrLeuHisProProLeuVal 910       920       930       940       950       960
TGGGAGAGGCCCACCAAGGTCCGGCTGCCTAAGCTGTATCTGAAACACCAAATGGACCTG
TrpGluArgProThrLysValArgLeuProLysLeuTyrLeuLysHisGlnMetAspLeu 970       980       990      1000      1010      1020
GTGGCCACCCTCAGCCAGCTGGGCCTGCAGGAGTTGTTCCAGGCCCCAGACCTGCGTGGG
ValAlaThrLeuSerGlnLeuGlyLeuGlnGluLeuPheGlnAlaProAspLeuArgGly 1030      1040      1050      1060      1070      1080
ATCTCCGAGCAGAGCCTGGTGGTGTCCGGCGTGCAGCATCAGTCCACCCTGGAGCTCAGC
IleSerGluGlnSerLeuValValSerGlyValGlnHisGlnSerThrLeuGluLeuSer 1090      1100      1110      1120      1130      1140
GAGGTCGGCGTGGAGGCGGCGGCGGCCACCAGCATTGCCATGTCCCGCATGTCCCTGTCC
GluValGlyValGluAlaAlaAlaAlaThrSerIleAlaMetSerArgMetSerLeuSer 1150      1160      1170      1180      1190      1200
TCCTTCAGCGTGAACCGCCCCTTCCTCTTCTTCATCTTCGAGGACACCACAGGCCTTCCC
SerPheSerValAsnArgProPheLeuPhePheIlePheGluAspThrThrGlyLeuPro 1210      1220      1230      1240      1250      1260
CTCTTCGTGGGCAGCGTGAGGAACCCCAACCCCAGTGCACCGCGGGAGCTCAAGGAACAG
LeuPheValGlySerValArgAsnProAsnProSerAlaProArgGluLeuLysGluGln 1270      1280      1290      1300      1310      1320
CAGGATTCCCCGGGCAACAAGGACTTCCTCCAGAGCCTGAAAGGCTTCCCCCGCGGAGAC
GlnAspSerProGlyAsnLysAspPheLeuGlnSerLeuLysGlyPheProArgGlyAsp 1330      1340      1350      1360      1370      1380
AAGCTTTTCGGCCCTGACTTAAAACTTGTGCCCCCCATGGAGGAGGATTACCCCCAGTTT
LysLeuPheGlyProAspLeuLysLeuValProProMetGluGluAspTyrProGlnPhe

1392
GGCAGCCCCAAG
GlySerProLys
```

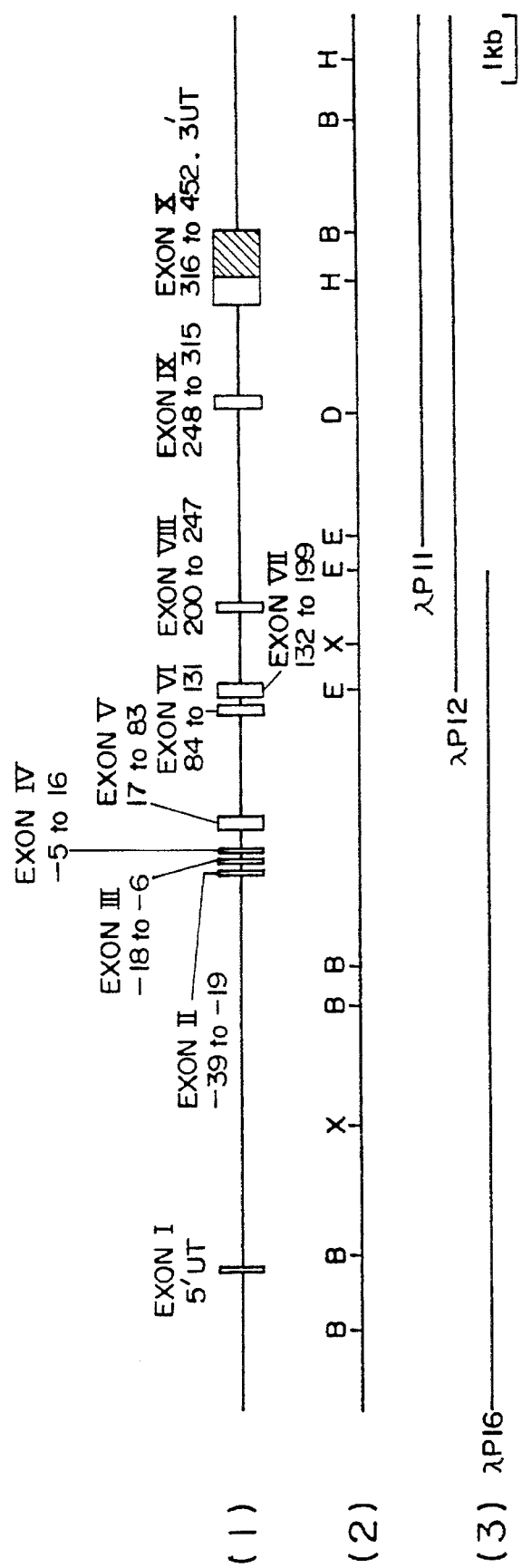

FIG. 4A

```
                                                                                EXON II    EXON III   EXON IV
                                                              -1 +1                        10
                                          CTT TCT GTC CCT GCC CAC AGG AAC ATG GCG CTG CTC
                                                                      Met Ala Leu Leu
       20              30              40              50              60
TGG GGC CTC CTG GTG CTC AGC TGG TCC TGC CTG CAA GGC CCC TGC GTG GTG AGC TGG TGA AGT GCA AGT
Trp Gly Leu Leu Val Leu Ser Trp Ser Cys Leu Gln Gly Pro Cys Val
                                                           -20
                                                                        intron 2
              70              80              90
CTT GCC ATG AGG AGG GCT TGG GAG CTC CGA GGG GAC CTC CTA TCC CTT TCT CCA CAG TTC TCC GTG AGC GCC ATG GAG CCC TTG GCC
                                                                      Phe Ser Pro Val Ser Ala Met Glu Pro Leu Gly Arg
                                                                                                                  -10
                                                   intron 3
          100
    Gln
CAG GTA CTG GGG AGT GAG GAG CCT GTG ATG GGG GGA AGG TCC CGG GGG TCT CAC TGG TGG GCA GGG TGG GGG GCC TGT GGG AAG GGT CGG
              110             120             130             140             150             160
TCT CCA TCT GCT TGC TCC TTT CCG CAG CTA ACT AGC CCG AAC CAG GAG CAG GTG TCC CCA CTT ACC CTC AAG TTG GCC AAC CAG GTA CAA
                                  Leu Thr Ser Pro Asn Gln Glu Gln Val Ser Pro Leu Thr Leu Lys Leu Gly Asn Gln
                                   -1 +1                                                   10
```

FIG. 4B

```
                                                                                          EXON V
CCA GGT GGG GCT GGG GAA GAG TGG GCG GGG CTA GAG GAG GGA GGA AGG GGT CGG GGG GTG GGG GCG CGT GCT GAG GCT CTG
                  170                 180                  190                 200                 210                 220                 230                 240
GAG TCC AGA GGC CAG AAG GGA AAG GGT GGG GAG GAC CGA GGC CCA GGC CCC AGA ATG CCA GTG CCC TCC CCC GTC TGA CGC CTC TTC CCT
                                       intron 4
GGG GCT GGG ACA AGG CCC TGC TGT CCT CAG GCA CAG GGG CTG TGA CAA GGC CTT CAA CAC AGA ACC TGG AGC TG   AC   CCC TTG ACC TCC CTG ACC
CCT GAT CTG TCC CTG CAG GAG CCT GGT GGC CAG ACT GCC CTG AAG AGT CCC CCA GAC GTC TGC AGA GAC CCA ACC CAG CAG ACC CAC AGG
                                      Glu Pro Gly Gly Gln Thr Ala Leu Lys Ser Pro Pro Val Cys Ser Arg Asp Pro Thr Gln Gln Thr His Arg
                                                          20                                        30                                        40
                250                 260                 270                 280                 290                 300                 310                 320                 330
CTG GCC CGG GCC ATG ATG GCC TTC ACT GCC GAC TTC TCC CTG GTG GCT CAA ACG TCC CCC AAC CTC ATC CTG TCA CCC CTG AGT GTG
Leu Ala Arg Ala Met Met Ala Phe Thr Ala Asp Phe Ser Leu Val Ala Gln Thr Ser Pro Asn Leu Ile Leu Ser Pro Leu Ser Val
                                                          50                                        60                                        70
340                 350                 360
GCC CTG GGG CTG TCT CAC CTG GCA CTA GGT ACC CTG GCA CCA CTT GTC CAG GAA CTC AGT ACT CCA CTG GTT CTC
Ala Leu Ala Leu Ser His Leu Ala Leu G
                80
```

FIG. 4C

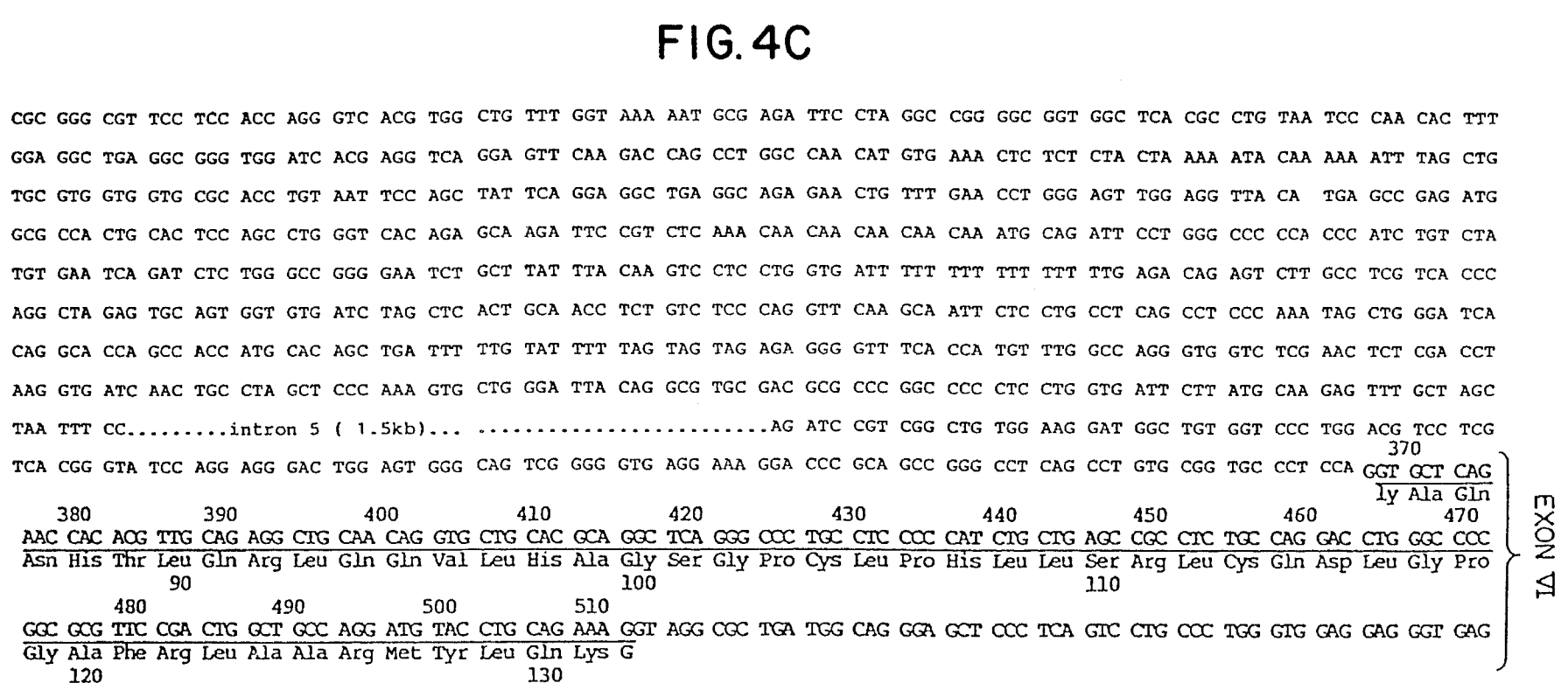

EXON VI

...Gly Ser Gly Val Leu His Ala Gly Pro His Leu Pro Cys Leu Arg Ser Gln Asp Leu Cys Gly Pro
100                                110                                    470
Asn His Thr Leu Gln Arg Leu Gln Gln Val Gln Gln Leu Cys His Leu Ser Arg Leu Cys Gly Pro
90
Gly Ala Phe Arg Leu Ala Ala Arg Met Tyr Leu Gln Lys Gly
120                                130 ly Ala Gln
470

FIG. 4D

```
                                                intron 6                                          EXON VII
AGC AAG GGG CTG GCC CTC TGG TAG CGA GTA GGG GCG TGT CTG GCT GTG GAG CCT GGA ACA GCT TGT GCT TCC GTG CAG  GA TTT
520       530           540           550           560           570           580           590           600    ly Phe
CCC ATC AAA GAA GAT TTC CTG GAA CAA CAG CTA TTT GGG GCA AAG CCC GTG AGC CTG ACG GAA CAG GAA GAT GAC CTG GCA AAC ATC      610
Pro Ile Lys Asp Phe Leu Glu Gln Gln Leu Phe Gly Ala Lys Pro Val Ser Leu Thr Glu Gln Glu Asp Asp Leu Ala Asn Ile
         140                         150                         160
AAC CAA TGG GTG AAG GAG GCC ACG GAG AAG ATT CAG G
620           630           640           650
Asn Gln Trp Val Lys Glu Ala Thr Glu Lys Ile Gln G
        170
```

PROTEIN HAVING HUMAN PLASMIN INHIBITING ACTIVITY

This application is a Continuation of now abandoned application, Ser. No. 08/060,691, filed May 13, 1993 which is a Continuation of abandoned application Ser. No. 07/419,913, filed Sep. 5, 1989.

This invention relates to a novel protein having the activity of inhibiting human plasmin, a process for production thereof by gene manipulation, and to its use in the field of pharmaceuticals.

Human $\alpha_2$ plasmin inhibitor (to be abbreviated as "$\alpha_2$-PI") was first isolated and purified by Aoki and Moroi. It is known to be a single-chain glycoprotein having a molecular weight of about 67,000 and containing 11.7% of saccharide chains which is a strong plasmin inhibitor capable of instantaneously inhibiting the esterase activity of plasmin, a fibrinolytic enzyme [see M. Moroi & N. Aoki: The Journal of Biological Chemistry, 251, 5956–5965 (1976)].

As proposed in EP 0292609 (Jun. 29, 1988), the present inventors isolated a complementary DNA (cDNA for short) of a human $\alpha_2$-plasmin inhibitor from a cDNA library of human liver cells, and determined the amino acid sequence of the human $\alpha_2$-plasmin inhibitor ($\alpha_2$-PI) from its structure.

Investigations of the present inventors have shown that a polypeptide having a much longer amino acid sequence than ordinary human $\alpha_2$-PI, which is shown in FIG. 1 attached to this application, has human plasmin inhibitory activity as human $\alpha_2$-PI, and that this polypeptide can be produced more efficiently than the ordinary human $\alpha_2$-PI from cells transfected by using a DNA fragment encoding the amino acid sequence of the above polypeptide. This has led to the accomplishment of this invention.

According to this invention, there is first provided a protein having human plasmin inhibiting activity, substantially equivalent reactivity with human plasmin to a human $\alpha_2$-plasmin inhibitor derived from plasma, a binding ability to human fibrin about ¼ to about ⅓ of that of the human $\alpha_2$-plasmin inhibitor derived from plasma, and a molecular weight of about 50,000 to about 77,000.

The protein provided by this invention is a "modified human $\alpha_2$-PI" formed mainly of substantially the same amino acid sequence portion as the mature protein of human $\alpha_2$-PI with a short-chain polypeptide being bound to the above amino acid sequence, and is characterized by having the following physiological activities.

(a) Its reactivity with human plasmin is substantially equivalent to that of human $\alpha_2$-PI derived from plasma (to be referred to as native human $\alpha_2$-PI), and (b) its ability to bind to human fibrin is about ¼ to about ⅓ of that of the native human $\alpha_2$-PI.

The reactivity of the protein with human plasmin, referred to herein, can be measured by the following procedure. The protein is incubated with human plasmin at 37° C. for a period of 30 seconds, 1 minute, 3 minutes or 5 minutes. ε-Aminocaproic acid is added, and the activity of the remaining human plasmin is measured by a method using a synthetic substrate S-2251.

When measured under the above conditions, the reactivity of the protein of this invention is within the range of 70 to 110%, especially 90 to 100% of that of native human $\alpha_2$-PI, and these reactivities are substantially equivalent to each other.

The ability of the protein to bind to human fibrin can be determined by measuring the amount of the $^{125}$I-labelled protein taken up into a fibrin clot by means of a gamma-counter. The binding ability of the protein of this invention is in the range of about ¼ to about ⅓ of that of native human $\alpha_2$-PI, and in this respect, the protein of this invention can be distinguished with the native human $\alpha_2$-PI.

The protein of this invention may contain a glycochain structural portion as the native human $\alpha_2$-PI does, but the inclusion of the glycochain structural portion is not essential. The protein of this invention may have a molecular weight of generally about 50,000 to about 77,000, preferably about 67,000 to about 70,000. Irrespective of whether or not the protein of this invention contains the glycochain structural portion, the polypeptide chain portion desirably has a molecular weight of about 50,000.

Generally, the protein of this invention has the following amino acid composition although it slightly varies depending upon the method of its production, etc.

| | |
|---|---|
| L-alanine | 5.5 to 7.9 mole % |
| L-arginine | 4.0 to 4.8 mole % |
| L-asparagine | 6.9 to 8.3 mole % |
| L-aspartic acid | |
| L-glutamine | 12.0 to 14.5 mole % |
| L-glutamic acid | |
| Glycine | 5.6 to 6.7 moole % |
| L-histidine | 2.1 to 2.8 mole % |
| L-isoleusine | 1.7 to 2.4 mole % |
| L-leusine | 14.2 to 16.8 mole % |
| L-lysine | 3.6 to 4.6 mole % |
| L-methionine | 1.8 to 2.7 mole % |
| L-phenylalanine | 5.6 to 7.0 mole % |
| L-proline | 8.0 to 9.0 mole % |
| L-serine | 7.0 to 8.6 mole % |
| L-threonine | 3.6 to 5.7 mole % |
| L-tyrosine | 0.6 to 1.5 mole % |
| L-valine | 5.8 to 6.6 mole % |

One specific example of the protein of this invention is a Pro-type human $\alpha_2$-PI resulting from binding of a peptide chain composed of 12 amino acids having the following amino acid sequence MetGluProLeuGlyArgGlnLeuThrSerGlyPro        [III]

to the N-terminus of human $\alpha_2$-PI.

The human $\alpha_2$-PI to which the above peptide chain is bound may be of the same protein structure as native human $\alpha_2$-PI derived from plasma, or of one resulting from removal one or more glycochain portions. It may also be of a structure resulting from replacement of at least one amino acid constituting the polypeptide chain portion of native human $\alpha_2$-PI by another amino acid to such an extent that the physiological activity of native human $\alpha_2$-PI is not substantially impaired, or of a structure resulting from bonding of one or more amino acids to the C-terminus of the polypeptide chain.

One specific preferred example of the Pro-type human $\alpha_2$-PI provided by this invention is one having the following amino acid sequence [I] resulting from binding of the amino acid sequence [III] to the N-terminus of native $\alpha_2$-PI.

1          10          20        [I]
MetGluProLeuGlyArgGlnLeuThrSerGlyProAsnGlnGluGlnValSerProLeu

```
                              30                         40
ThrLeuLeuLysLeuGlyAsnGlnGluProGlyGlyGlnThrAlaLeuLysSerProPro 50                         60
GlyValCysSerArgAspProThrProGluGlnThrHisArgLeuAlaArgAlaMetMet 70                         80
AlaPheThrAlaAspLeuPheSerLeuValAlaGlnThrSerThrCysProAsnLeuIle 90                        100
LeuSerProLeuSerValAlaLeuAlaLeuSerHisLeuAlaLeuGlyAlaGlnAsnHis 110                        120
ThrLeuGlnArgLeuGlnGlnValLeuHisAlaGlySerGlyProCysLeuProHisLeu 130                        140
LeuSerArgLeuCysGlnAspLeuGlyProGlyAlaPheArgLeuAlaAlaArgMetTyr 150                        160
LeuGlnLysGlyPheProIleLysGluAspPheLeuGluGlnSerGluGlnLeuPheGly 170                        180
AlaLysProValSerLeuThrGlyLysGlnGluAspAspLeuAlaAsnIleAsnGlnTrp 190                        200
ValLysGluAlaThrGluGlyLysIleGlnGluPheLeuSerGlyLeuProGluAspThr 210                        220
ValLeuLeuLeuLeuAsnAlaIleHisPheGlnGlyPheTrpArgAsnLysPheAspPro 230                        240
SerLeuThrGlnArgAspSerPheHisLeuAspGluGlnPheThrValProValGluMet 250                        260
MetGlnAlaArgThrTyrProLeuArgTrpPheLeuLeuGluGlnProGluIleGlnVal 270                        280
AlaHisPheProPheLysAsnAsnMetSerPheValValLeuValProThrHisPheGlu 290                        300
TrpAsnValSerGlnValLeuAlaAsnLeuSerTrpAspThrLeuHisProProLeuVal 310                        320
TrpGluArgProThrLysValArgLeuProLysLeuTyrLeuLysHisGlnMetAspLeu 330                        340
ValAlaThrLeuSerGlnLeuGlyLeuGlnGluLeuPheGlnAlaProAspLeuArgGly 350                        360
IleSerGluGlnSerLeuValValSerGlyValGlnHisGlnSerThrLeuGluLeuSer 370                        380
GluValGlyValGluAlaAlaAlaAlaThrSerIleAlaMetSerArgMetSerLeuSer 390                        400
SerPheSerValAsnArgProPheLeuPhePheIlePheGluAspThrThrGlyLeuPro 410                        420
LeuPheValGlySerValArgAsnProAsnProSerAlaProArgGluLeuLysGluGln 430                        440
GlnAspSerProGlyAsnLysAspPheLeuGlnSerLeuLysGlyPheProArgGlyAsp 450                        460
LysLeuPheGlyProAspLeuLysLeuValProProMetGluGluAspTyrProGlnPhe

464
GlySerProLys
```

A glycochain structural portion may be bonded to at least one amino acid out of the 99th Asn, 268th Asn, 282nd Asn, 289th Asn and 410th Asn in the above amino acid sequence. Preferably, the glycochain structural portion is of the same type as that bonded to the native human $\alpha_2$-PI.

The protein of this invention having human plasmin inhibiting activity may be produced, for example, in accordance with a gene manipulation technique by inserting a DNA fragment encoding the protein of this invention into a suitable expression vector, transforming animal cells as a host with the recombinant vector, and culturing the resulting transformed cells. The DNA fragment encoding the protein of this invention may be isolated from human chromosomes IS. Hirosawa et al.: Proc. Natl. Acad. Sci., U.S.A., 85, 6836–6840 (1988)], or one semi-synthesized from messenger RNA, isolated from human cells, as a template [Y. Sumi et al., J. Biochem., 100, 1299–1402 (1986)], or one purely synthesized in accordance with the amino acid sequence of the polypeptide portion of the protein of this invention.

One specific example of the DNA fragment is a DNA fragment having the following DNA sequence [II] (the amino acid sequence is simultaneously indicated herein) encoding the above amino acid sequence [I].

```
          10        20        30        40        50        60      [II]
ATGGAGCCCTTGGGCCGGCAGCTAACTAGCGGGCCGAACCAGGAGCAGGTGTCCCCACTT
Met Glu Pro Leu Gly Arg Gln Leu Thr Ser Gly Pro Asn Gln Glu Gln Val Ser Pro Leu 70        80        90       100       110       120
ACCCTCCTCAAGTTGGGCAACCAGGAGCCTGGTGGCCAGACTGCCCTGAAGAGTCCCCCA
Thr Leu Leu Lys Leu Gly Asn Gln Glu Pro Gly Gly Gln Thr Ala Leu Lys Ser Pro Pro 130       140       150       160       170       180
GGAGTCTGCAGCAGAGACCCCACCCCAGAGCAGACCCACAGGCTGGCCCGGGCCATGATG
Gly Val Cys Ser Arg Asp Pro Thr Pro Glu Gln Thr His Arg Leu Ala Arg Ala Met Met 190       200       210       220       230       240
GCCTTCACTGCCGACCTGTTCTCCCTGGTGGCTCAAACGTCCACCTGCCCCAACCTCATC
Ala Phe Thr Ala Asp Leu Phe Ser Leu Val Ala Gln Thr Ser Thr Cys Pro Asn Leu Ile 250       260       270       280       290       300
CTGTCACCCCTGAGTGTGGCCCTGGCGCTGTCTCACCTGGCACTAGGTGCTCAGAACCAC
Leu Ser Pro Leu Ser Val Ala Leu Ala Leu Ser His Leu Ala Leu Gly Ala Gln Asn His 310       320       330       340       350       360
ACGTTGCAGAGGCTGCAACAGGTGCTGCACGCAGGCTCAGGGCCCTGCCTCCCCCATCTG
Thr Leu Gln Arg Leu Gln Gln Val Leu His Ala Gly Ser Gly Pro Cys Leu Pro His Leu 370       380       390       400       410       420
CTGAGCCGCCTCTGCCAGGACCTGGGCCCCGGCGCGTTCCGACTGGCTGCCAGGATGTAC
Leu Ser Arg Leu Cys Gln Asp Leu Gly Pro Gly Ala Phe Arg Leu Ala Ala Arg Met Tyr 430       440       450       460       470       480
CTGCAGAAAGGATTTCCCATCAAAGAAGATTTCCTGGAACAATCCGAACAGCTATTTGGG
Leu Gln Lys Gly Phe Pro Ile Lys Glu Asp Phe Leu Glu Gln Ser Glu Gln Leu Phe Gly 490       500       510       520       530       540
GCAAAGCCCGTGAGCCTGACGGGAAAGCAGGAAGATGACCTGGCAAACATCAACCAATGG
Ala Lys Pro Val Ser Leu Thr Gly Lys Gln Glu Asp Asp Leu Ala Asn Ile Asn Gln Trp 550       560       570       580       590       600
GTGAAGGAGGCCACGGAGGGGAAGATTCAGGAATTCCTCTCTGGGCTGCCGGAAGACACC
Val Lys Glu Ala Thr Glu Gly Lys Ile Gln Glu Phe Leu Ser Gly Leu Pro Glu Asp Thr 610       620       630       640       650       660
GTGTTGCTTCTCCTCAACGCCATCCACTTCCAGGGTTTCTGGAG,AACAAGTTTGACCCG
Val Leu Leu Leu Leu Asn Ala Ile His Phe Gln Gly Phe Trp Arg Asn Lys Phe Asp Pro 670       680       690       700       710       720
AGCCTTACCCAGAGAGACTCCTTCCACCTGGACGAGCAGTTCACGGTGCCCGTGGAAATG
Ser Leu Thr Gln Arg Asp Ser Phe His Leu Asp Glu Gln Phe Thr Val Pro Val Glu Met 730       740       750       760       770       780
ATGCAGGCCCGCACGTACCCGCTGCGCTGGTTCTTGCTGGAGCAGCCTGAGATCCAGGTG
Met Gln Ala Arg Thr Tyr Pro Leu Arg Trp Phe Leu Leu Glu Gln Pro Glu Ile Gln Val 790       800       810       820       830       840
GCTCATTTCCCCTTTAAGAACAACATGAGCTTTGTGGTCCTTGTACCCACCCACTTTGAA
Ala His Phe Pro Phe Lys Asn Asn Met Ser Phe Val Val Leu Val Pro Thr His Phe Glu 850       860       870       880       890       900
TGGAACGTGTCCCAGGTACTGGCCAACCTGAGTTGGGACACCCTGCACCCACCTCTGGTG
Trp Asn Val Ser Gln Val Leu Ala Asn Leu Ser Trp Asp Thr Leu His Pro Pro Leu Val 910       920       930       940       950       960
TGGGAGAGGCCCACCAAGGTCCGGCTGCCTAAGCTGTATCTGAAACACCAAATGGACCTG
Trp Glu Arg Pro Thr Lys Val Arg Leu Pro Lys Leu Tyr Leu Lys His Gln Met Asp Leu 970       980       990      1000      1010      1020
GTGGCCACCCTCAGCCAGCTGGGCCTGCAGGAGTTGTTCCAGGCCCCAGACCTGCGTGGG
Val Ala Thr Leu Ser Gln Leu Gly Leu Gln Glu Leu Phe Gln Ala Pro Asp Leu Arg Gly 1030      1040      1050      1060      1070      1080
ATCTCCGAGCAGAGCCTGGTGGTGTCCGGCGTGCAGCATCAGTCCACCCTGGAGCTCAGC
Ile Ser Glu Gln Ser Leu Val Val Ser Gly Val Gln His Gln Ser Thr Leu Glu Leu Ser
```

```
                1090          1100          1110          1120          1130                1140
          GAGGTCGGCGTGGAGGCGGCGGCGGCCACCAGCATTGCCATGTCCCGCATGTCCCTGTCC
          Glu  Val Gly Val Glu Ala Ala Ala Ala Thr Ser Ile Ala Met Ser Arg Met Ser Leu Ser 1150          1160          1170          1180          1190                1200
          TCCTTCAGCGTGAACCGCCCCTTCCTCTTCTTCATCTTCGAGGACACCACAGGCCTTCCC
          Ser Phe Ser Val Asn Arg Pro Phe Leu Phe Phe Ile Phe Glu Asp Thr Thr Gly Leu Pro 1210          1220          1230          1240          1250                1260
          CTCTTCGTGGGCAGCGTGAGGAACCCCAACCCCAGTGCACCGCGGGAGCTCAAGGAACAG
          Leu Phe Val Gly Ser Val Arg Asn Pro Asn Pro Ser Ala Pro Arg Glu Leu Lys Glu Gln 1270          1280          1290          1300          1310                1320
          CAGGATTCCCCGGGCAACAAGGACTTCCTCCAGAGCCTGAAAGGCTTCCCCCGCGGAGAC
          Gln Asp Ser Pro Gly Asn Lys Asp Phe Leu Gln Ser Leu Lys Gly Phe Pro Arg Gly Asp 1330          1340          1350          1360          1370                1380
          AAGCTTTTCGGCCCTGACTTAAAACTTGTGCCCCCCATGGAGGAGGATTACCCCAGTTT
          Lys Leu Phe Gly Pro Asp Leu Lys Leu Val Pro Pro Met Glu Glu Asp Tyr Pro Gln Phe

1392
          GGCAGCCCCAAG
          Gly Ser Pro Lys
```

In this DNA sequence, at least one intron may be interposed in this DNA sequence as in the $\alpha_2$-PI DNA fragment derived from human chromosomes. In the above DNA fragment, the codons may be replaced by other codons so long as they code the same amino acids.

One specific example of the DNA fragment is a hybrid DNA fragment obtained by linking a ca. 2600 base pair (bp for short) human $\alpha_2$-PI chromosomal DNA fragment (FIG. 4) ranging from the 5'-terminus of exon VII to the restriction endonuclease EcoRI site at the 141st base from the 5'-terminus, which contains a region ranging from the 5'-terminus of the exon VII-downstream to the restriction endonuclease AluI site 20 bp upstream of exon (VII) of the human $\alpha_2$-PI chromosomal DNA in FIG. 3, with a ca. 1.7 kbp cDNA fragment of human $\alpha_2$ in FIG. 5 ranging from the restriction endonuclease EcoRI site on the 5' upstream side to the EcoRI linker binding site on the 3' downstream side by the method shown in FIG. 6.

The DNA fragment coding for the protein of this invention is inserted into an expression vector properly selected according to the host-vector system. Specific examples of such an expression vector include pSV2-neo, pSV3-neo, pSV5-neo, pSV2-gpt, pSV2-dhfr, pSVK, pSVL, pSVLT47, HomerVI, pSVELL9, pMSV1472, pJYMMT, pLTN3, pKCR and pAdD26SV(A)3. Among them, pSV2-neo, pSV2-gpt and pSV2dhfr are preferred.

The insertion of the DNA fragment into the vector may be carried out by methods known per se, for example the method described in O. Miura et al., J. Clin. Invest., 83, 1598–1604 (1989).

The animal cells as a host may be cells of man or other animals, for example BHK (hamster kidney cells), CHO (Chinese hamster ovary), 293 (human kidney cells), Chang Liver (human liver cells), and HeLa (human cervical carcinoma cells). Of these, BHK cells are conveniently used.

Transfection of these animal cells into the expression vectors may be carried out by methods well known in the art, for example the methods described in D. A. Spandidos and N. M. Wilkie: Expression of Exogenous DNA in Mammalian Cells; and B. D. Hames and S. J. Higgins edited: Transcription and Translation, IRL Press, Oxford, pp. 1–48.

The resulting transformed cells are cultured in a customary manner under conditions adapted to the respective cells, and the protein of this invention can be recovered from the culture.

The reactivity of the protein of this invention with human plasmin is substantially equivalent to native human $\alpha_2$-PI, and the protein of this invention is expected to be used, for example, as an anti-clotlysis agent. It is also useful for $\alpha_2$-PI supplying therapy to $\alpha_2$-PI-deficient patients and for supplying $\alpha_2$-PI to patients with hepatic diseases whose hepatic function is reduced.

When the protein of this invention is to be used in such pharmaceutical applications, the protein of this invention may be formulated into a suitable dosage form together with a suitable solid or liquid carrier or diluent.

The protein of this invention may be formulated into a form suitable for administration, for example an injectable solution, a drip, a lyophilized powder, together with a pharmaceutically acceptable carrier or diluent. Examples of the pharmaceutically acceptable carrier or diluent are water, buffers, blood isotonizing agents, stabilizers (e.g., human plasma albumin, mannitol), and human antibodies or their fragments. The injectable solution or the drip may be prepared by dissolving the protein of this invention in physiological saline in a concentration of 0.01 microgram/ml to 1 mg/ml, and as required, further adding 0.01M sodium phosphate as a buffer, and 1% of mannitol and 0.1% of human serum albumin as stabilizers. The concentrations of the additional agents may be varied properly. As required, a human antibody or its fragment may be added. The injectable solution or drip may be prepared in the form of a solution or a lyophilized form. The lyophilized product may be dissolved in such a medium as pure water before use. The injectable solution, the drip, a lyophilized product thereof, and a solution of the lyophilized product should be prepared and stored aseptically.

The protein of the invention may be administered parenterally, preferably intravenously. The dose varies depending upon the sex, age, condition, body weight, etc. of a patient to be treated. Generally, the dose may be about 0.01 to about 10 mg/kg of body weight daily as an amount effective for dissolving thrombus either once or several times a day. By the judgment of a physician, it may, of course, be administered in higher doses.

The following examples illustrate in detail cloning of human $\alpha_2$-PI cDNA, cloning of human $\alpha_2$-PI chromosomal gene, construction of an expression vector for the protein of this invention having plasmin inhibiting activity, transfection of the novel plasmin-inhibiting protein into animal cells, purification of the novel plasmin inhibiting protein, the method of determining the structure of amino terminals, and the activity of the novel plasmin inhibiting protein.

The drawings cited in the following examples have the following meanings.

FIGS. 1A and 1B show the primary structure of one example of the protein of this invention having plasmin inhibiting activity.

FIGS. 2A and 2B are one example of the DNA sequence coding for the protein having plasmin inhibiting activity shown in FIGS. 1A and 1B, which is given with the corresponding amino acid sequence of the protein.

FIG. 3 shows a human $\alpha_2$-plasmin inhibitor chromosomal gene.

FIG. 3, (1) shows introns and exons of a human $\alpha_2$-plasmin inhibitor-genome gene. The ten exons are shown by rectangular markings.

FIG. 3, (2) shows a restriction endonuclease map of human $\alpha_2$-plasmin inhibitor-genome gene. The restriction endonucleases are indicated by abbreviations as follows:- B: BamHI, D:DraI, E: EcoRI, H: HindIII, X:XhoI.

FIG. 3, (3) shows three DNA fragments in phage clones coding for the human $\alpha_2$-plasmin inhibitor-genome gene used in this invention. FIGS. 3, (1) to (3) vertically correspond to each other.

FIGS. 4A, 4B, 4C and 4D show one example of a chromosomal gene fragment inserted into an expression vector.

Figure 5:
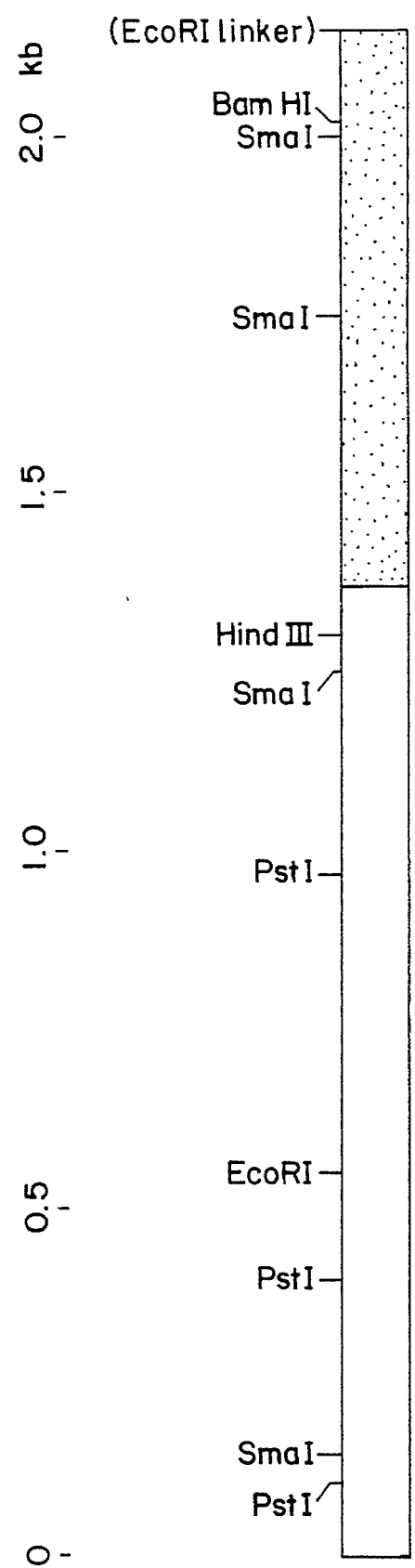

FIG. 5 is a restriction endonuclease map of an about 2.2 kg human $\alpha_2$-plasmin inhibitor-cDNA. The black portion indicates a non-coding region.

Figure 6:
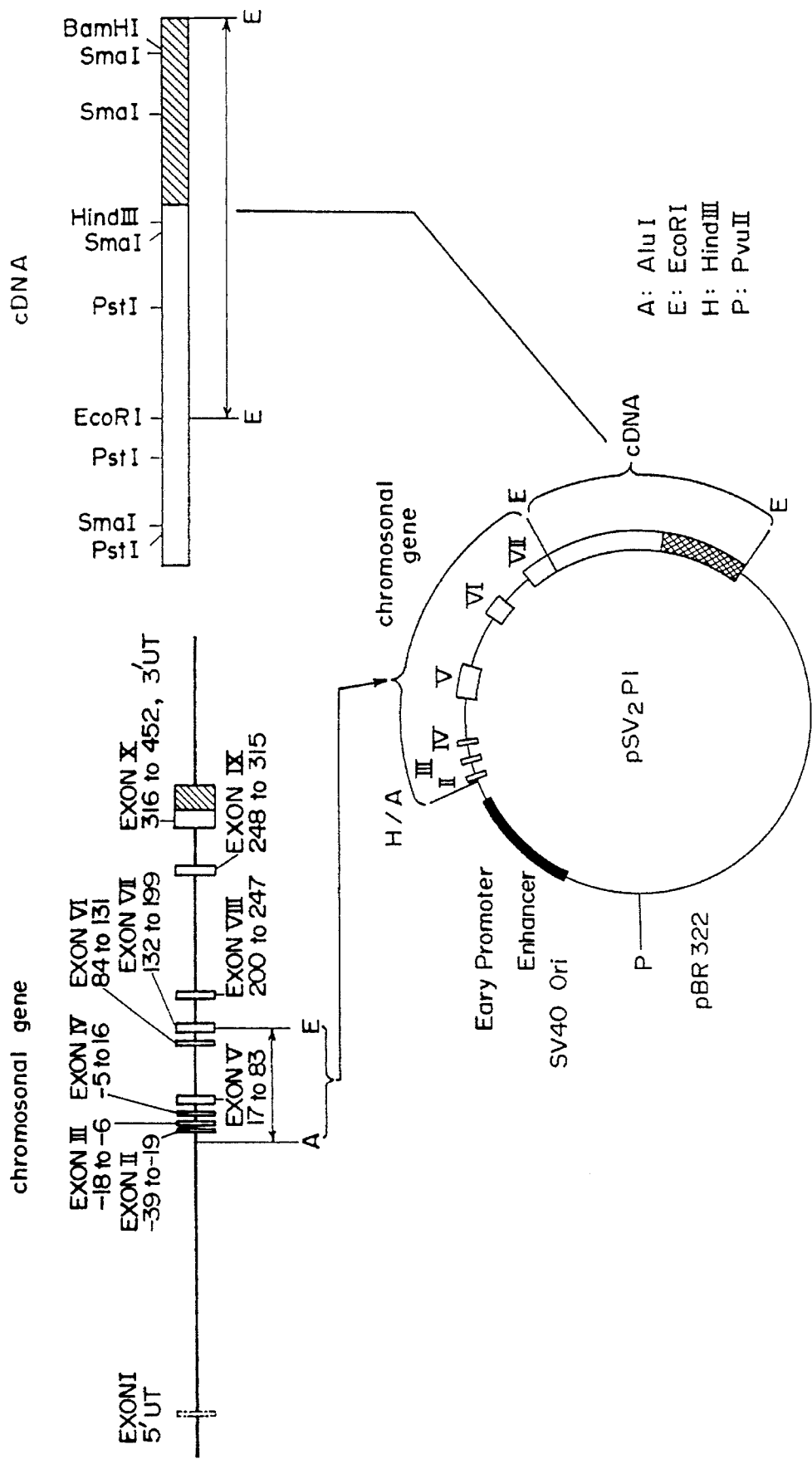

FIG. 6 shows a method of linking a genome DNA fragment and a cDNA fragment. The following symbols stand for the restriction endonucleases indicated. A:AluI, E: EcoRI, H: HindIII, P: PstI.

Figure 7:
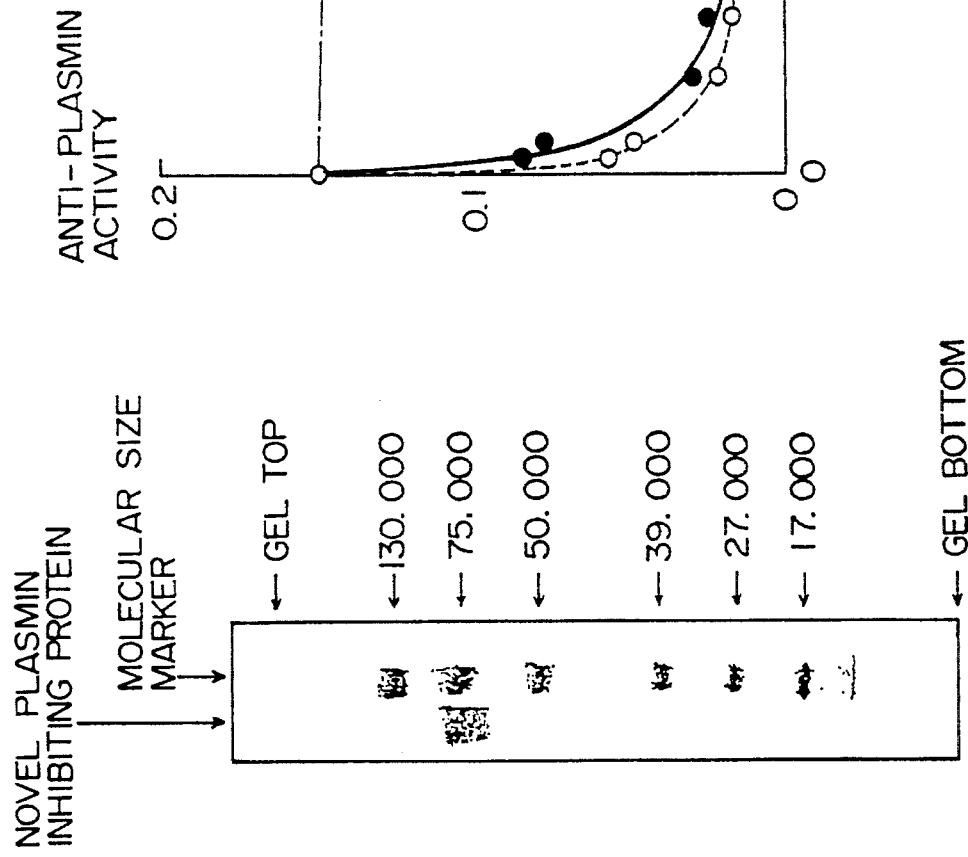

FIG. 7 shows an SDS-polyacrylamide gel electrophoretic pattern of the protein of this invention having plasmin inhibiting activity. The molecular size markers were phosphorylase b (130,000), bovine serum albumin (75,000), ovalbumin (50,000), carbonic anhydrase (39,000), soybean trypsin inhibitor (27,000), lysozyme (17,000), respectively, from the gel top.

Figure 8:
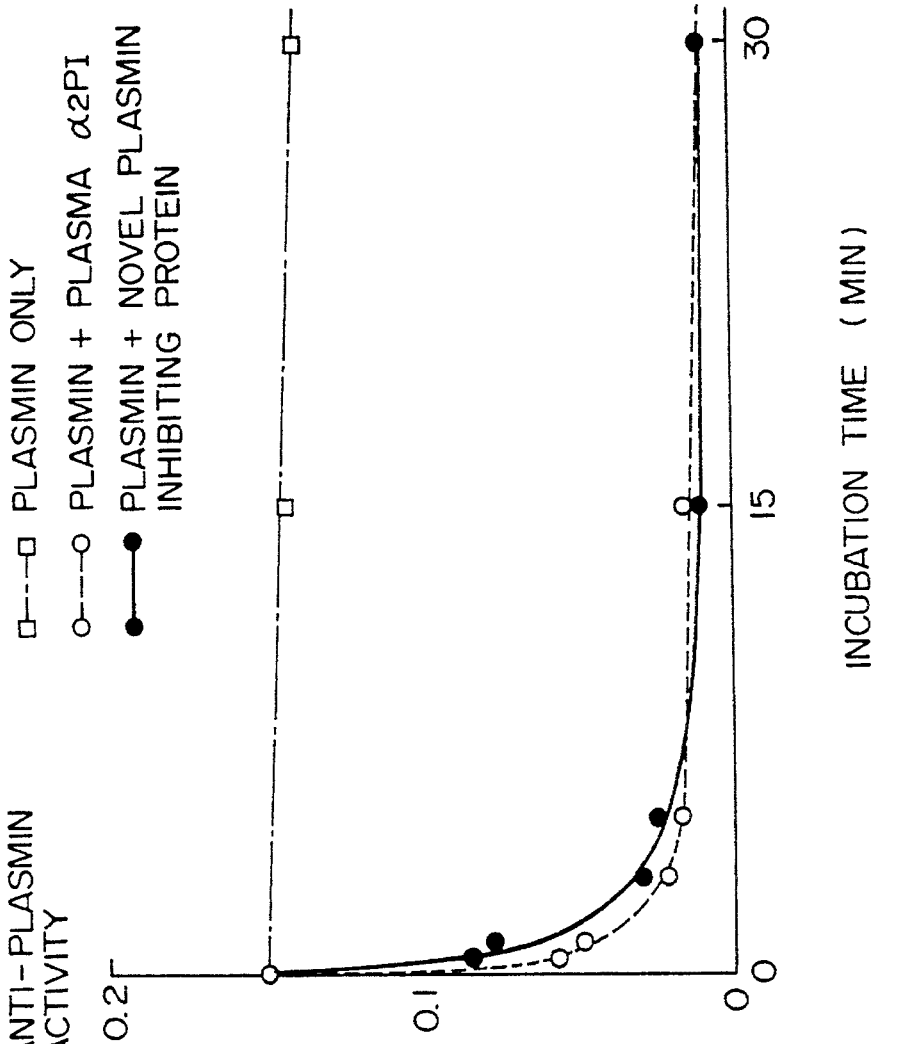

FIG. 8 shows the plasmin inhibiting activity of the novel plasmin inhibiting protein. The axis of abscissas represents the incubation time (minutes) and the axis of ordinates, the degree of decompositon of the substrate by the residual plasmin expressed as a change in absorbance per minute at 405 nm. □——□ shows the results with plasmin alone; ○ ··· ○, the results with a plasmin/plasma $\alpha_2$-PI system; and ●——●, the results with a plasmin/novel plasmin inhibiting protein system.

Figure 9:
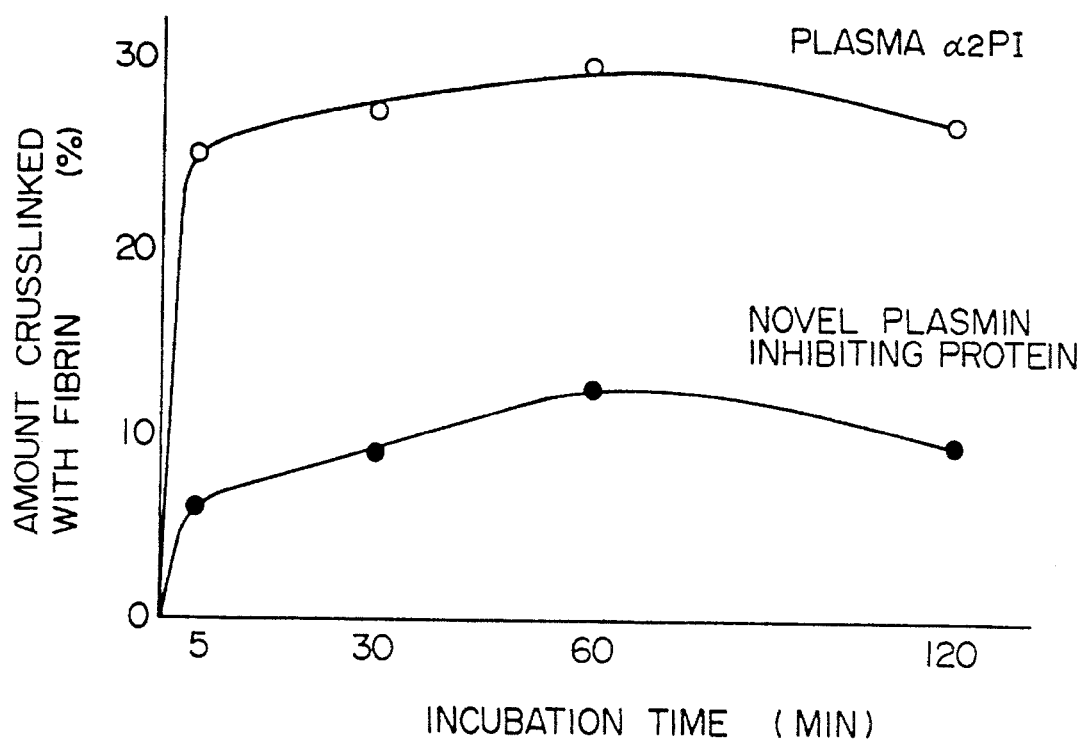
Figure 11:
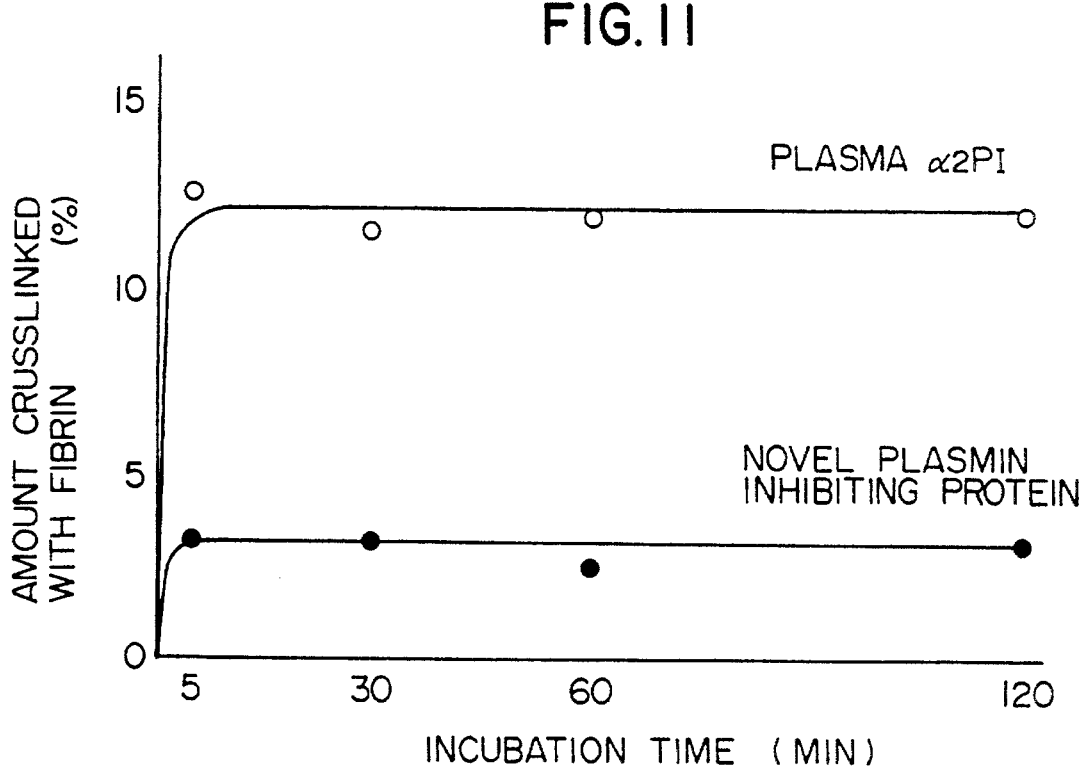
Figure 10:
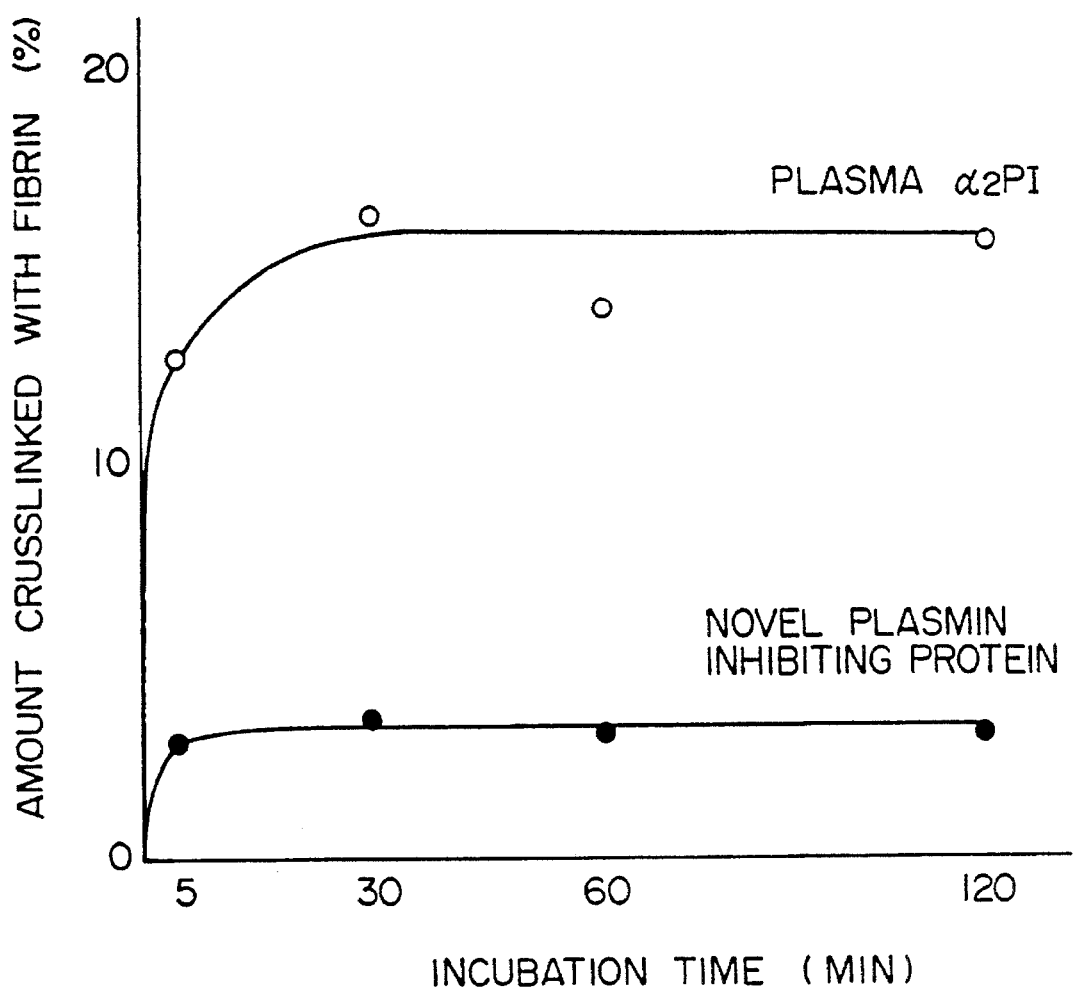

FIGS. 9, 10 and 11 show the results of measurement of the crosslinking ability of the novel plasmin-inhibiting protein to fibrin. The axis of abscissas represents the incubation time (minutes); and the axis of ordinates, the proportion in % of the protein in the added $^{125}$I-labelled protein which crosslinked with fibrin. ○—○ shows plasma $\alpha_2$-PI, and ●—● the novel plasmin inhibiting protein.

It should be understood that in the present invention and drawings, amino acids and polypeptides are abbreviated by the method adopted by IUPAC-IUB Biochemical Committee (CBN).

The DNA sequence will be indicated by using the following abbreviations for bases contained in the deoxyribonucleotides in the DNA sequence.

A: adenine (representing deoxyadenylic acid)

C: cytosine (representing deoxycytidylic acid)

G: guanine (deoxyguanilic acid)

T: thymine (deoxythymidylic acid)

EXAMPLE 1

Screening of human $\alpha_2$-plasmin inhibitor

A cDNA library derived from human liver cells using λgt10 as a vector was infected with E. coli C600hfl⁻ to form plaques. Clones containing human $\alpha_2$-plasmin inhibitor genes were screened by the plaque hybridization method of Benton and Davis [see W. D. Benton & R. W. Davis: Science, 196, 180 (1977)] using [$^{32}$P]-labelled probes. The synthetic DNAs used as the probe were synthesized by means of a DNA synthesizer (made by Applied Biosystems) and had the following DNA sequences corresponding to the partial amino acid sequence of human $\alpha_2$-plasmin inhibitor which was reported by Collen et al. [see D. Collen et al.: Thrombosis and Haemostasis, 48, 311–314 (1982)].

```
(P-1)  Met  Glu  Glu  Asp  Tyr  Pro
  3'   TAC  CTT  CTT  CTG  ATG  GG 5'
              C    C    A    A (P-2)  Val  Glu  Het  Met  Gln  Ala
  3'   CAG  TCT  TAC  TAC  GTT  CG 5'
        A    C              C
        T
        C
```

The symbols given below the DNA sequences of P-1 and P-2 means that they can independently replace the bases indicated above.

λgt10 DNA containing the human $\alpha_2$-plasmin inhibitor cDNA was digested with EcoRI to cut out the inserted human $\alpha_2$-plasmin inhibitor and isolated by 0.8% agarose gel electrophoresis. The resulting human $\alpha_2$-PI-cDNA fragment (0.1 μg) was dissolved in 10 microliters of a buffer for digestion with a restriction endonuclease [an aqueous solution containing 100 mM NaCl, 50 mM Tris-HCl (pH 7.5), 10 mM MgCl$_2$ and 1 mM dithiothreitol for digestion with EcoRI; an aqueous solution containing 50 mM NaCl, 10 mM Tris-HCl (pH 7.5), 10 mM MgCl$_2$ and 1 mM dithiothreitol for digestion with BamHI, PstI and HindIII; and an aqueous solution containing 20 mM KCl, 10 mM Tris-HCl (pH 8.0), 10 mM MgCl$_2$ and 1 mM dithiothreitol for digestion with Sma I]. Two units of a restriction endonuclease (a product of Takara Shuzo Co., Ltd.) was added to the solution to digest the human $\alpha_2$-PI cDNA fragment at 37° C. for 1 hour.

When two kinds of restriction endonucleases are used in the digestion, it is carried out first with a restriction endonuclease which acts at a low salt concentration. Then the salt concentration is raised, and the digestion is then carried out with a restriction endonuclease which acts at the higher salt concentration.

After the digestion with the restriction endonuclease, one microliter of an aqueous solution containing 0.25% bromophenol blue and 50% glycerol was added, and gel electrophoresis was carried out using 0.8%–1.2% agarose containing 1 μg/ml of ethidium bromide. At the time of electrophoresis, a product obtained by digesting λphage DNA with HindIII was used as a molecular size marker. After the electrophoresis, the gel was irradiated with ultraviolet rays, and the digestion pattern was observed. Digestion patterns obtained by the restriction endonucleases used singly, and those obtained by two or more restriction endonucleases were analyzed, and the relative positions of the restriction endonuclease cleavage sites to be described were determined. The obtained restriction endonuclease map of the human $\alpha_2$-PI cDNA fragment is shown in FIG. 5.

Plasmid pUC8 for E. coli (2 μg) was digested with restriction endonuclease EcoRI, and then reacted with 1.0 unit of alkaline phosphatase (E. coli C75) (a product of Takara Shuzo Co., Ltd.) at 58° C. for 2 hours. After the reaction, the reaction solution was extracted three times with phenol to deactivate and remove the alkaline phosphatase in it. The human $\alpha_2$-PI derived from λgt10 DNA/EcoRI cDNA fragment was added to the resulting alkaline phosphatase-treated solution of pUC8 digested with EcoRI, and the mixture was reacted with 2 units of T4-DNA ligase at 12° C. for 16 hours to link the plasmid with the DNA fragment.

E. coli LE392 was transformed in accordance with an ordinary $CaCl_2$ method [M. V. Norgard et al.: Gene, 3, 297 (1978)] with hybrid DNA obtained by linking an about 1.7 kb cDNA fragment obtained by digesting the human $\alpha_2$-PI DNA with EcoRI with the above pUC8. The transformed E. Coli LE392 was inoculated in an L-broth plate containing ampicillin in a concentration of 50 μg/ml. The plate was incubated overnight at 37° C. to grow the transformants. DNAs were prepared from the resulting colonies by using a known method. By agarose gel electrophoresis, the desired DNAs were identified, and one of them was named pP139.

EXAMPLE 2

Cloning of human $\alpha_2$-PI-genome gene

DNA extracted from human placenta was digested with restriction endonucleases AluI and HaeIII, and then via an EcoRI linker, incorporated in Charon 4A bacterio-phage vector to construct a library. This library ($1.2 \times 10^6$ plaques) was screened by the method of Benton-Davis [W. D. Benton & R. W. Davis: Science 196, 180–182 (1977)] using as a probe a cDNA fragment corresponding to an amino acid sequence ranging from 31st to 130th amino acids and from the 179th to 429th amino acids counted from the N-terminus of the $\alpha_2$-PI. For screening the clone on the 3' upstream side, synthetic DNA composed of 15 bases (5' ACTCCCCTGC-CAGCC 3') was used as the probe. When cDNA was used as the probe, the cDNA fragment was labelled with [$^{32}$P] by nick translation. The synthetic DNA was labelled on the 5' side with [$^{32}$P] using T4 polynucleotide kinase.

As a result of screening, three clones, λP11, λP12 and λP16, which encode the entire region of the $\alpha_2$-PI chromosomal gene, were obtained. The correspondence of these clones to the chromosomal genes are shown in FIGS. 3, (1) to (3).

EXAMPLE 3

Preparation of an expression vector for a novel plasmin inhibiting protein

Plasmid pP139 obtained in Example 1 was digested with restriction endonuclease EcoRI by a method similar to that shown in Example 1 to isolate a human $\alpha_2$-PI cDNA fragment (1.7 kbp) (see FIG. 5).

On the other hand, the human $\alpha_2$-PI chromosomal gene clone λP16 was digested with EcoRI to cut out the inserted human $\alpha_2$-PI chromosomal gene and isolate it by 0.9–1.5% agarose gel electrophoresis. A fragment (about 2.6 kbp) containing exons II, III, IV, V, VI and part of VII of the human $\alpha_2$ plasmin inhibitor chromosomal gene ranging from restriction endonuclease AluI 30 bp on the 5' upstream side of exon II of the human $\alpha_2$-PI chromosomal gene to restriction endonuclease EcoRI 141 bp from 5'-upstream portion of exon VII was obtained (see FIG. 4).

The human $\alpha_2$-PI cDNA fragment (about 1.7 kbp) obtained above was linked with the fragment (about 2.6 kbp) containing exons II, III, IV, V, VI and part of VII of the human $\alpha_2$-PI chromosomal gene by means of a ligase. The expression vector pSV2 was digested with restriction endonuclease HindIII, smoothed by Klenow polymerase, and further digested with restriction endonuclease EcoRI. The digestion product was ligated with the above DNA obtained by ligation by means of a ligase, and the ligation product was transfected into E. coli C600. From the resulting expression vectors, an expression vector in which the human $\alpha_2$-PI chromosomal gene and the human $\alpha_2$-PI cDNA were linked in a direction to correctly encode human $\alpha_2$-PI and expressed the novel plasmin inhibiting protein was selected by preparing a restriction endonuclease map. Thus, expression vector pSV2PI for expressing the novel plasmin inhibiting protein shown in FIG. 6 was obtained.

EXAMPLE 4

Transfection of the vector capable expressing the novel plasmin inhibiting protein into BHK cells The transfection of the expression vector into BHK cells was carried out by using Cell Phect Transfection Kit made by Pharmacia Co. in accordance with the protocol therein.

Ten micrograms of the expression vector pSV2PI and 30 micrograms of the selection marker expression vector pSV2-DHFR were dissolved in 120 microliters of distilled water, and 120 microliters of buffer A was added. After the mixture was stirred, it was left to stand at room temperature for 10 minutes. To this solution was quickly added 240 microliters of buffer B, and the mixture was left to stand at room temperature for 15 minutes. This solution was added to BHK-21 (C-13) cells being cultured in a Petri dish with a diameter of 10 cm. The BHK cells were incubated at 37° C. for 6 hours in the presence of 5% $CO_2$. The culture supernatant was removed and to the residue were added 2 ml of 15% glycerol and HEPES buffer (pH 7.5). The mixture was left to stand at room temperature for 3 minutes. The supernatant was removed, and the residue was washed with D-MEM containing 5 ml of 10% FCS (fetal calf serum), and 10 ml of SD-MEM containing 10% FCS was added. Incubation was carried out at 37° C. in the presence of 5% $CO_2$.

After the lapse of 48 hours, the cells were peeled from the plate, and diluted so that the number of the cells decreased to about ½ to about 1/50. Then, the cells were cultured in Dulbecco's MEM medium containing 250 nM of methotrexate and 10% FCS. In about 2 weeks, several tens of colonies were obtained. The colonies were isolated, and the amount of the human $\alpha_2$-PI antigen in the culture supernatant of the cells was measured. Thus, novel plasmin inhibiting protein-producing cell clone BHK-PI 10 was obtained.

EXAMPLE 5

Transfection of the expression vector into CHO cells

The transfection of the expression vector into CHO cells was carried out by using Cell Phect Transfection Kit made by Pharmacia Co. in accordance with the protocol therein.

Ten micrograms of the expression vector pSV2PI and 30 micrograms of the selection marker expression vector pSV2-DHFR were dissolved in 120 microliters of distilled water, and 120 microliters of buffer A was added. After the mixture was stirred, it was left to stand at room temperature for 15 minutes. To this solution was quickly added 240 microliters of buffer B, and the mixture was left to stand at room temperature for 15 minutes. The solution was added to CHO-K1 cells being cultivated in a Petri dish with a diameter of 10 cm. The CHO-K1 cells were incubated at 37° C. for 6 hours in the presence of 5% $CO_2$, and the culture supernatant was removed. To the residue were added 2 ml of 15% glycerol and HEPES buffer (pH 7.5). The mixture was left to stand at room temperature for 3 minutes. The supernatant was removed, and the residue was washed with D-MEM containing 5 ml of 10% FCS (fetal calf serum), and 10 ml of SD-MEM containing 10% FCS was added. Incubation was carried out at 37° C. in the presence of 5% $CO_2$.

After the lapse of 48 hours, the cells were peeled from the plate, and diluted so that the number of the cells decreased to about ½ to about ⅟50. Then, the cells were cultured in Dulbecco's MEM medium containing 250 nM of methotrexate and 10% FCS. In about 2 weeks, several tens of colonies were obtained. The colonies were isolated, and the amount of the human $\alpha_2$-PI antigen in the culture supernatant of the cells was measured. Thus, novel plasmin inhibiting protein-producing cell clone CHO-PI15 was obtained.

EXAMPLE 6

Transfection of the expression vector into 293 cells

The transfection of the expression vector into 293 cells was carried out by using Cell Phect Transfection Kit made by Pharmacia Co. in accordance with the protocol therein.

Ten micrograms of the expression vector pSV2PI and 30 micrograms of the selection marker expression vector pSV2-DHFR were dissolved in 120 microliters of distilled water, and 120 microliters of buffer A was added. After the mixture was stirred, it was left to stand at room temperature for 10 minutes. To this solution was quickly added 240 microliters of buffer B, and the mixture was left to stand at room temperature for 15 minutes. The solution was added to 293 cells being cultivated in a Petri dish with a diameter of 10 cm. The 293 cells were incubated at 37° C. for 6 hours in the presence of 5% $CO_2$, and the culture supernatant was removed. To the residue were added 2 ml of 15% glycerol and HEPES buffer (pH 7.5). The mixture was left to stand at room temperature for 3 minutes. The supernatant was removed, and the residue was washed with D-MEM containing 5 ml of 10% FCS (fetal calf serum), and 10 ml of SD-MEM containing 10% FCS was added. Incubation was carried out at 37° C. in the presence of 5% $CO_2$.

After the lapse of 48 hours, the cells were peeled from the plate, and diluted so that the number of the cells decreased to about ½ to about ⅟50. Then, the cells were cultured in Dulbecco's MEM medium containing 250 nM of methotrexate and 10% FCS. In about 2 weeks, several tens of colonies were obtained. The colonies were isolated, and the amount of the human $\alpha_2$-PI antigen in the culture supernatant of the cells was measured. Thus, novel plasmin inhibiting protein-producing cell clone 293-PI3 was obtained.

EXAMPLE 7

Transfection of the expression vector into Chang-Liver cells

The transfection of the expression vector into Chang-Liver cells was carried out by using Cell Phect Transfection Kit made by Pharmacia Co. in accordance with the protocol therein.

Ten micrograms of the expression vector pSV2PI and 30 micrograms of the selection marker expression vector pSV2-DHFR were dissolved in 120 microliters of distilled water, and 120 microliters of buffer A was added. After the mixture was stirred, it was left to stand at room temperature for 10 minutes. To this solution was quickly added 240 microliters of buffer B, and the mixture was left to stand at room temperature for 15 minutes. The solution was added to Chang-Liver cells being cultivated in a Petri dish with a diameter of 10 cm. The Chang-Liver cells were incubated at 37° C. for 6 hours in the presence of 5% $CO_2$, and the culture supernatant was removed. To the residue were added 2 ml of 15% glycerol and HEPES buffer (pH 7.5). The mixture was left to stand at room temperature for 3 minutes. The supernatant was removed, and the residue was washed with D-MEM containing 5 ml of 10% FCS (fetal calf serum), and 10 ml of SD-MEM containing 10% FCS was added. Incubation was carried out at 37° C. in the presence of 5% $CO_2$.

After the lapse of 48 hours, the cells were peeled from the plate, and diluted so that the number of the cells decreased to about ½ to about ⅟50. Then, the cells were cultured in Dulbecco's MEM medium containing 250 nM of methotrexate and 10% FCS. In about 2 weeks, several tens of colonies were formed. The colonies were isolated, and the amount of the human $\alpha_2$-PI antigen in the culture supernatant of the cells was measured. Thus, novel plasmin inhibiting protein-producing cell clone CL-PI6 was obtained.

EXAMPLE 8

Purification of the novel plasmin inhibiting protein and the termination of its structure at the amino terminals The novel plasmin inhibiting protein was purified by affinity chromatography using a monoclonal antibody to the human $\alpha_2$-PI in accordance with the method described in Japanese Laid-Open Patent Publication No. 91527/1986.

The cells BHK-PI10, CHO-PI15, 293-PI3 and CL-sPI6 having the ability to produce the novel plasmin-inhibiting protein obtained in Examples 4, 5 and 6 were each cultured in Dulbecco's MEM medium containing 10% FCS. 250 ml of the culture was concentrated to about 30 ml by a protein concentrator (Amicon Concentrator). The concentrate was applied to a column of an anti-$\alpha_2$ plasmin monoclonal antibody. The column was well washed with PBS (pH 7.6) and then eluted by 5M guanidine hydrochloride (pH 7.4). The eluate was immediately dialyzed against PBS (pH 7.6) three times to purify the plasmin-inhibiting protein. The purified protein was electrophoresed on an SDS-polyacrylamide gel. It showed a single band as shown in FIG. 7, and was determined to have a molecular weight of about 67,000 to 70,000.

The amino acid sequence of the purified plasmin-inhibiting protein (10 micrograms) from the amino terminal was analyzed by a protein sequencer (Protein Sequencer 477) and a PTH analyzer (PTH Analyzer 120A) (both made by Applied Biosystems Co.). The results are shown in Table 1.

TABLE 1

| Cycle number | Detected amino acid |
| --- | --- |
| 1 | Met |
| 2 | Glu |
| 3 | Pro |
| 4 | Leu |
| 5 | Gly |

TABLE 1-continued

| Cycle number | Detected amino acid |
| --- | --- |
| 6 | Arg |
| 7 | Glu |
| 8 | Leu |
| 9 | Thr |
| 10 | Ser |
| 11 | Gly |
| 12 | Pro |
| 13 | Asn |
| 14 | Gln |

EXAMPLE 9

Plasmin inhibiting activity (I) of the novel plasmin inhibiting protein

A mixture of 0.025 unit of plasminogen and 0.031 unit of urokinase, which had been incubated at 37° C. for 30 minutes, was added to 1 microliter of the novel plasmin-inhibiting protein purified in Example 8 or plasma $\alpha_2$-PI, and the total amount of the mixture was adjusted to 40 microliters. A portion (10 microliters) of the mixture was placed on a fibrin plate (made by Daiichi Chemicals Co., Ltd.). The fibrin plate was left to stand for 18 hours at a temperature of 37° C. and a humidity of more than 95%, and the dissolved area was measured. Furthermore, 2.5 micrograms of a monoclonal antibody JTPI-1 which recognizes, and binds to, the neighborhood of the reactive sites of $\alpha_2$-PI was mixed with 1 microgram of the novel plasmin-inhibiting protein or plasma $\alpha_2$-PI, and the mixture was incubated at 37° C. for 30 minutes. Then 20 microliters of a mixture of 0.025 unit of plasminogen and 0.031 unit of urokinase, which had previously been incubated at 37° C. for 30 minutes, was added, and the amount of the mixture was adjusted to 40 miroliters. A portion (10 microliters) of the mixture was placed on a fibrin plate. The fibrin plate was left to stand for 18 hours at a temperature of 37° C. and a humidity of more than 95%. The dissolved area was measured. The results are shown in Table 2.

TABLE 2

| | Dissolved area (mm²) |
| --- | --- |
| Plasmin alone | 22.0 |
| Plasmin + plasma $\alpha_2$-PI | 0.0 |
| Plasmin + novel plasmin inhibiting protein | 0.0 |
| Plasmin + plasma $\alpha_2$-PI + JTPI-1 | 17.1 |
| Plasmin + novel plasmin inhibiting protein + JTPI-1 | 26.1 |

EXAMPLE 10

Plasmin inhibiting activity (II) of the novel plasmin-inhibiting protein

Three microliters of the novel plasmin inhibiting protein solution (7.14 micromoles/liter) purified in Example 8, 100 microliters of a plasmin solution (0.03 casein unit/liter) and 400 microliters of Tris buffer (Tris 0.05 mole/liter, NaCl 0.14 moles/liter pH 7.6, NaCl 0.14 mole/liter pH 7.6) was mixed. After the lapse of 0 second, 30 seconds, 1 minute, 3 minutes, 5 minutes, 15 minutes and 30 minutes, respectively, 50 microliters of epsilon-aminocaproic acid (0.1 mole/liter) and 100 microliters of S-2251 (3.4 mmoles/liter; a product of Daiichi Chmicals, Co., Ltd.) were added. The degree of decomposition of the substrate by the remaining plasmins was measured by a spectrophotometer (DU-64). The results are shown in FIG. 8. The novel plasmin-inhibiting proteins and plasma $\alpha_2$-PI showed nearly equivalent plasmin inhibiting activity.

EXAMPLE 11

Labelling of protein with $^{125}I$

Plasma $\alpha_2$-PI and the novel plasmin-inhibiting proteins were labelled with $^{125}I$ by the method of J. Mimuro et al. [see J. Mimuro et al.: J. Clin. Invest., 77, 1006–1013 (1986)] using beads (Enzymobead, a product of Bio-Rad) having a lactoperoxidase and glucooxidase solidified herein and Na $^{125}I$ (13 mCi/µg: Amersham).

$\alpha_2$-PI (100 micrograms) derived from plasma and 36 micrograms of the novel plasmin-inhibitingprotein of this invention were each reacted with Enzymobead and 0.1% β-D-glucose in the presence of 0.5 mCi of Na $^{125}I$ at room temperature for 30 minutes to incorporate $^{125}I$. The reaction was stopped by adding 5 microliters of 10% $NaN_3$, and the reaction solution was charged on a PD-10 column (Pharmacia) to separate it into 0.5 ml fractions. One microliter of each of the fractions were subjected a gamma-counter to determine the amount of gamma-rays. The amount of the protein in each fraction was determined by measuring the absorbance of the fraction at 280 nm. As a result, 47 micrograms of plasma $\alpha_2$-PI having a specific radioactivity of 0.70 µCi/µg and 12.5 micrograms of the novel plasmin inhibiting protein having a specific radioactivity of 1.92 µCi/µg were obtained.

EXAMPLE 12

Measurement of the ability to bind to fibrin by crosslinking (I)

The abilities of the plasma $\alpha_2$-PI and the novel plasmin inhibiting protein of the invention to crosslink with fibrin were measured by the method of Mimuro et al. [see J. Mimuro et al.: J. Clin. Invest., 77, 1006–1013 (1986)]. Five microliters of calcium chloride (50 mM) and 10 microliters of a thrombin solution (20 units/ml) were added to 85 microliters of a mixed solution of 250 micrograms of fibrinogen, 0.6 microgram of the $^{125}I$-labelled novel plasmin inhibiting protein or $^{125}I$-labelled plasma $\alpha_2$-PI and 1 unit of aprotinin to start coagulation. After incubation at 37° C. for 5, 30, 60 or 120 minutes, 100 microliters of 0.2M EDTA solution was added to stop the reaction. The resulting product was well unravelled with a bamboo stick, and well washed three times with 1 ml of a 50 mM Tris buffered saline (to be abbreviated as TBS) containing 2 mM EDTA and 1 mM iodoacetamide. The amount of gamma-rays in the coagulated product was measured by a gamma-counter. The results are shown in FIG. 9. It was found that the ability of the novel plasmin inhibiting protein to crosslink with fibrin was 25 to 40% of that of plasma $\alpha_2$-PI.

EXAMPLE 13

Measurement of the ability to crosslink with fibrin (II)

The same experiment as in Example 12 was carried out using plasma as a source of fibrinogen. Five microliters of calcium chloride (50 mM) and 10 microliters of a thrombin solution (2 units/ml) were added to 85 microliters of a mixed solution of 60 microliters of normal human plasma, 0.6 microgram of $^{125}$I-labelled novel plasmin inhibiting protein or $^{125}$-labelled plasma $\alpha_2$-PI, and 1 unit of aprotinin to start coagulation. After incubation at 37° C. for 5, 30, 60 or 120 minutes, 100 microliters of a 0.2M EDTA solution was added to stop the reaction. The reaction product was well unravelled with a bamboo stick, and well washed three times with 1 ml of 50 mM TBS containing 2 mM EDTA and 1 mM iodoacetamide three times. The amount of gamma-rays in the resulting coagulated product was measured by a gamma-counter. The results are shown in FIG. 10. It was found that the ability of the novel plasmin inhibiting protein to crosslink with fibrin was 20 to 22% of that of plasma $\alpha_2$-PI.

EXAMPLE 14

Determination of the ability to crosslink with fibrin (III)

The same experiment as in Examples 12 and 13 was carried out using as a source of fibrinogen plasma from which $\alpha_2$-PI was removed. The $\alpha_2$-PI-removed plasma was obtained by applying plasma to a column to which an anti-$\alpha_2$-PI monoclonal antibody was fixed, and passing it through the column. The amount of $\alpha_2$-PI in the $\alpha_2$-PI-removed plasma was determined to less than 0.1 μg/ml. Five microliters of calcium chloride (50 mM) and 10 microliters of a thrombin solution (20 units/ml) were added to 85 microliters of a mixed solution containing 60 microliters of $\alpha_2$-PI-removed plasma and 0.6 microgram of $^{125}$I-labelled novel plasmin inhibiting protein or $^{125}$I-labelled plasma $\alpha_2$-PI to start coagulation. 100 microliters of a 0.2M EDTA solution was added to stop the reaction. The reaction product was well unravelled with a bamboo stick, and well washed three times with 1 ml of 50 mM TBS containing 2 mM EDTA and 1 mM iodoacetamide. The amount of gamma-rays in the coagulated product was measured by a gamma-counter. The results are shown in FIG. 11. It was found that the ability of the novel plasmin inhibiting protein to crosslink with fibrin was 20 to 27% of that of the plasma $\alpha_2$-PI.

We claim:

1. An isolated, substantially pure recombinant protein having human plasmin inhibiting activity of about 70 to 110% of the reactivity with human plasmin to human $\alpha_2$-plasmin inhibitor derived from plasma, capable of binding to human fibrin at a level of about ¼ to about ⅓ of that of the human $\alpha_2$-plasmin inhibitor derived from plasma, when measured by the amount of $I^{125}$ labelled protein taken up into a fibrin clot, by means of a gamma-counter, and a molecular weight of about 50,000 to about 77,000.

2. The protein of claim 1 in which a polypeptide chain portion has a molecular weight of about 50,000.

3. The protein of claim 1 in which a peptide chain having the following amino acid sequence MetGluProLeuGlyArgGlnLeuThrSerGlyPro is bound to the N-terminus of the human $\alpha_2$-plasmin inhibitor.

4. The protein of claim 1 which has the following amino acid sequence:

[I]

```
1                          10                           20
MetGluProLeuGlyArgGlnLeuThrSerGlyProAsnGlnGluGlnValSerProLeu 30                           40
ThrLeuLeuLysLeuGlyAsnGlnGluProGlyGlyGlnThrAlaLeuLysSerProPro 50                           60
GlyValCysSerArgAspProThrProGluGlnThrHisArgLeuAlaArgAlaMetMet 70                           80
AlaPheThrAlaAspLeuPheSerLeuValAlaGlnThrSerThrCysProAsnLeuIle 90                           100
LeuSerProLeuSerValAlaLeuAlaLeuSerHisLeuAlaLeuGlyAlaGlnAsnHis 110                           120
ThrLeuGlnArgLeuGlnGlnValLeuHisAlaGlySerGlyProCysLeuProHisLeu 130                           140
LeuSerArgLeuCysGlnAspLeuGlyProGlyAlaPheArgLeuAlaAlaArgMetTyr 150                           160
LeuGlnLysGlyPheProIleLysGluAspPheLeuGluGlnSerGluGlnLeuPheGly 170                           180
AlaLysProValSerLeuThrGlyLysGlnGluAspAspLeuAlaAsnIleAsnGlnTrp 190                           200
ValLysGluAlaThrGluGlyLysIleGlnGluPheLeuSerGlyLeuProGluAspThr 210                           220
ValLeuLeuLeuLeuAsnAlaIleHisPheGlnGlyPheTrpArgAsnLysPheAspPro 230                           240
SerLeuThrGlnArgAspSerPheHisLeuAspGluGlnPheThrValProValGluMet 250                           260
MetGlnAlaArgThrTyrProLeuArgTrpPheLeuLeuGluGlnProGluIleGlnVal
```

```
                                              -continued
                   270                       280
AlaHisPheProPheLysAsnAsnMetSerPheValValLeuValProThrHisPheGlu 290                       300
TrpAsnValSerGlnValLeuAlaAsnLeuSerTrpAspThrLeuHisProProLeuVal 310                       320
TrpGluArgProThrLysValArgLeuProLysLeuTyrLeuLysHisGlnMetAspLeu 330                       340
ValAlaThrLeuSerGlnLeuGlyLeuGlnGluLeuPheGlnAlaProAspLeuArgGly 350                       360
IleSerGluGlnSerLeuValValSerGlyValGlnHisGlnSerThrLeuGluLeuSer 370                       380
GluValGlyValGluAlaAlaAlaAlaThrSerIleAlaMetSerArgMetSerLeuSer 390                       400
SerPheSerValAsnArgProPheLeuPhePheIlePheGluAspThrThrGlyLeuPro 410                       420
LeuPheValGlySerValArgAsnProAsnProSerAlaProArgGluLeuLysGluGln 430                       440
GlnAspSerProGlyAsnLysAspPheLeuGlnSerLeuLysGlyPheProArgGlyAsp 450                       460
LysLeuPheGlyProAspLeuLysLeuValProProMetGluGluAspTyrProGlnPhe 464
GlySerProLys.
```

5. The protein of claim 1 which can be produced by BHK-21 (C-13) cells into which pSV2PI is introduced.

6. A pharmaceutical composition comprising an effective amount of the protein of claim 1 and a carrier or diluent.

7. A method of inhibiting human plasmin activity in a patient in need of such inhibition which comprises administering a human plasmin inhibiting amount of the protein of claim 1 to such patient.

\* \* \* \* \*